(12) United States Patent
Zupp et al.

(10) Patent No.: US 9,033,687 B2
(45) Date of Patent: May 19, 2015

(54) HOSE PUMP WITH PLANETARY GEAR

(75) Inventors: Andre Zupp, Dessau (DE); Uwe Schwerdtfeger, Amesdorf (DE)

(73) Assignee: ULRICH GMBH & CO. KG, Ulm (DE)

( * ) Notice: Subject to any disclaimer, the term of this patent is extended or adjusted under 35 U.S.C. 154(b) by 371 days.

(21) Appl. No.: 13/581,682

(22) PCT Filed: Dec. 23, 2010

(86) PCT No.: PCT/EP2010/070714
§ 371 (c)(1),
(2), (4) Date: Nov. 19, 2012

(87) PCT Pub. No.: WO2011/107179
PCT Pub. Date: Sep. 9, 2011

(65) Prior Publication Data
US 2013/0071270 A1 Mar. 21, 2013

(30) Foreign Application Priority Data

Mar. 1, 2010 (DE) .......................... 10 2010 000 592

(51) Int. Cl.
*F04B 43/12* (2006.01)
*A61M 5/142* (2006.01)
*F04B 43/08* (2006.01)

(52) U.S. Cl.
CPC ............ *F04B 43/12* (2013.01); *A61M 5/14232* (2013.01); *F04B 43/08* (2013.01); *F04B 43/1253* (2013.01)

(58) Field of Classification Search
CPC ...................................................... F04B 43/12
USPC ............... 417/474, 476, 477.1, 477.3, 477.4, 417/477.6
See application file for complete search history.

(56) References Cited

U.S. PATENT DOCUMENTS 3,216,362 A * 11/1965 Hewko .......................... 417/475
3,358,609 A * 12/1967 Worth et al. ............... 417/477.6
(Continued)

FOREIGN PATENT DOCUMENTS

AT        367874 B     8/2007
DE        7113125       4/1971
(Continued)

OTHER PUBLICATIONS

International Search Report for PCT/EP2010/070714 published Sep. 9, 2011.
(Continued)

*Primary Examiner* — Devon Kramer
*Assistant Examiner* — Patrick Hamo
(74) *Attorney, Agent, or Firm* — Fleit Gibbons Gutman Bongini & Bianco PL; Martin Fleit; Paul D. Bianco

(57) ABSTRACT

The invention relates to a hose pump for delivering a medium conveyed through a hose, including a housing, a drive, a carrier rotatable with respect to the housing, and a plurality of squeeze rollers that are mounted rotatably on the carrier and can be driven by the drive via a gear with a sun wheel and with a first planet wheel connected so as to rotate with the respective squeeze roller, wherein rotating squeeze rollers, during operation of the pump, press a hose, which is inserted into the pump, by squeezing the hose against an abutment and in this way convey the medium onwards through the hose in the delivery direction. In order to permit easier and quicker insertion of a hose in such a hose pump, the invention proposes that, in addition to the first planet wheel, each squeeze roller is also assigned at least a second planet wheel, which is coupled to the inner circumference, acting as a hollow wheel, of the housing in order to set the carrier in rotation from the drive during operation of the pump.

15 Claims, 5 Drawing Sheets

(56) References Cited

U.S. PATENT DOCUMENTS

| | | | |
|---|---|---|---|
| 3,749,531 A * | 7/1973 | Walker et al. | 418/45 |
| 4,604,038 A | 8/1986 | Belew | |
| 4,997,347 A * | 3/1991 | Roos | 417/475 |
| 5,387,088 A * | 2/1995 | Knapp et al. | 417/53 |
| 5,871,341 A * | 2/1999 | Melody | 417/477.6 |
| 5,941,696 A * | 8/1999 | Fenstermacher et al. | 417/477.6 |
| 6,685,450 B2 | 2/2004 | Bandis et al. | |
| 6,852,181 B2 | 2/2005 | Wheeler, Jr. | |
| 2002/0071776 A1 | 6/2002 | Bandis et al. | |
| 2003/0111143 A1 | 6/2003 | Wheeler, Jr. | |
| 2005/0129545 A1 * | 6/2005 | Prosek, Jr. | 417/474 |
| 2011/0185758 A1 | 8/2011 | Shimokawa et al. | |

FOREIGN PATENT DOCUMENTS

| | | |
|---|---|---|
| EP | 2357878 A2 | 8/2011 |
| FR | 2071238 | 9/1971 |
| WO | 0225112 A1 | 3/2002 |

OTHER PUBLICATIONS

International Preliminary Report published Sep. 3, 2012 for PCT/EP2010/070714.

Written Opinion published Sep. 1, 2012 for PCT/EP2010/070714.

* cited by examiner

HOSE PUMP WITH PLANETARY GEAR

FIELD OF THE INVENTION

The invention pertains to a hose pump.

Such hose pumps are used in particular in medical engineering, for example, as an infusion pump or in injection and dialysis devices. A hose pump of the initially described type is described, for example, in AT 367 874. This publication describes a hose pump with several rollers that can be driven by a central part via a planetary gear, wherein the rollers roll on at least one hose that carries the medium to be conveyed and squeeze its free cross during this process. The rollers are rotatably arranged on a rotatably supported carrier and at least part of their circumference is frictionally engaged with the central part while they contact the hose. The hose pump comprises a shaft that is connected to the central part in a rotationally rigid fashion and can be driven by a motor. The central part features two circumferential grooves, in which elastically deformable rubber rings are held, wherein these rubber rings contact the outer circumference of the rollers and frictionally drive these rollers similar to a planetary gear when the central part rotates. The carrier, on which the rollers are rotatably supported, is composed of two discs that are rotatably supported on the central part at an axial distance from one another. When the shaft is driven by the motor, the rollers are also set in rotation by the central part via the rubber rings. The hoses contact an abutment and are squeezed against this abutment by the rollers such that the volume enclosed between two squeeze points is conveyed onward in the hose while the rollers roll on the hoses during the operation of the pump.

BACKGROUND OF THE INVENTION

The insertion of a hose into this known hose pump proves to be complicated and time-consuming because the hose or the hoses respectively need to be elaborately threaded between the outer circumference of the rollers and the abutment.

Based on these circumstances, the invention aims to additionally develop a hose pump of the initially described type in such a way that a simpler and faster insertion of a hose into the hose pump can be achieved. The threading of the hose preferably is realized automatically with the aid of an integrated threading device, in particular, while the pump is running.

These objectives are attained with the hose pump shown and described herein. Preferred embodiments of the inventive hose pump are also disclosed herein.

SUMMARY OF THE INVENTION

In the inventive hose pump, a simpler and faster insertion of a hose between the squeeze rollers and the abutment can be achieved while the pump is running by assigning a first planet wheel and a second planet wheel to each squeeze roller, wherein the first planet wheel of each squeeze roller is coupled to a sun wheel that is rotatively driven by a drive in order to set the squeeze rollers in rotation while the pump is running, and wherein the respective second planet wheel of each squeeze roller is coupled to the inner circumference of the housing that acts as crown wheel. Due to this arrangement, the carrier and the squeeze rollers rotatably supported thereon are set in rotation while the pump is running. Due to the rotation of the carrier relative to the housing, a hose can be easily threaded into the hose pump between the squeeze rollers and the abutment by inserting the hose or a hose end into the intake side of the hose pump. Due to the rotation of the carrier, the squeeze roller situated closest to the inserted hose is moved in the direction of the inserted hose such that the hose is squeezed between the outer circumference of this squeeze roller and the abutment and pulled further into the hose pump due to the static friction on the hose surface. Since the carrier continues to rotate relative to the housing, this is also realized accordingly with the remaining squeeze rollers until the hose is completely pulled into the hose pump.

The invention is based on the notion that a hose can be automatically threaded into the hose pump due to the fact that the carrier and the squeeze rollers supported thereon rotate while the pump is running, namely even if the hose is not yet inserted. In the initially described hose pump according to the prior art, the carrier only rotates if a hose is already inserted between the squeeze rollers and the abutment. In order to also realize a rotation of the carrier and of the squeeze rollers supported on the carrier when the hose is not yet inserted, the invention proposes to equip each squeeze roller with a first planet wheel and a second planet wheel, wherein the first planet wheel is directly coupled to the sun wheel and sets the squeeze roller in rotation and the second planet wheel transmits the torque of the sun wheel to the carrier via the inner circumference of the stationary housing that acts as crown wheel and consequently can also set the carrier in rotation while the pump is running if no hose is inserted.

In a preferred exemplary embodiment, the carrier is realized in the form of a carrier disk and rotatably supported on a driveshaft of the drive by means of a bearing. The squeeze rollers preferably are respectively arranged on a squeeze roller shaft that is rotatably supported in the carrier disk. In this case, the two planet wheels of each squeeze roller are mounted in a rotationally rigid fashion on the respective squeeze roller shaft at an axial distance from one another. The first planet wheel of each squeeze roller preferably is in contact with the sun wheel via a toothing such that the first planet wheel respectively transmits the torque of the sun wheel to the squeeze roller assigned to the first planet wheel in order to set the squeeze rollers in rotation while the pump is running. The toothing makes it possible to transmit higher torques. The second planet wheel of each squeeze roller is in contact with the inner circumference of the housing and rolls on the inner circumference of the housing while the pump is running such that the torque of the sun wheel is transmitted to the carrier disk via the second planet wheel of each squeeze roller. For this purpose, the squeeze rollers are respectively arranged and rotatably supported on the periphery of the carrier disk.

If a hose is not yet inserted into the pump, the drive drives the sun wheel and the planet wheels transmit the torque of the sun wheel to the squeeze rollers that rotate with the peripheral speed defined by the friction rollers. The carrier disk is simultaneously set in rotation because the friction wheel or the friction wheels roll on the inner circumference of the stationary housing that acts as crown wheel.

If a hose is inserted into the pump, the motor drives the sun wheel and the sun wheel transmits the torque to the squeeze rollers via the planet wheels. In this case, the friction wheels no longer have any effect because they slip on the inner circumference of the housing. The torque is directly transmitted from the sun wheel to the squeeze rollers that roll on the surface of the inserted hose and squeeze the hose against the abutment. This once again causes the carrier disk to be set in rotation. The peripheral speed of the squeeze rollers is adjusted to an ideal value in this case. In this way, the hose is prevented, in particular, from being pushed in front of the squeeze roller with the rotary motion of the carrier disk due to an excessively fast roller speed. At (excessively) slow roller speed, in contrast, the hose is not pressed "back" opposite to the rotary motion of the carrier disk. In both instances, undue stress on the hose and frictional losses are prevented such that the same pumping capacity can be achieved if the motor of the inventive pump is operated with reduced power.

The second planet wheel of each squeeze roller is preferably realized in the form of a toothless friction wheel that rolls on the likewise toothless or smooth inner circumference of the housing. For this purpose, each second planet wheel preferably features a ring of an elastomer material (such as, for example, a rubber O-ring) on its outer circumference, wherein each second planet wheel is frictionally engaged with the inner circumference of the housing by means of said ring. An optimal peripheral speed of the carrier disk and the squeeze rollers is automatically adjusted due to the relatively low frictional force between the friction wheel and the inner circumference of the housing that acts as crown wheel.

In order to realize the automatic threading of a hose into the hose pump, a preferred exemplary embodiment is provided with a threading device that automatically threads a hose into the hose pump between the outer circumference of the squeeze rollers and the abutment while the pump is running. The threading device preferably comprises a screw spindle that can be rotatively driven by a spindle drive. The spindle drive is preferably coupled to the drive of the pump in such a way that the spindle drive sets the screw spindle in rotation as soon as the drive of the pump sets the carrier disk in rotation. In order to thread a hose into the hose pump, it is merely required to insert a hose or a hose end into the screw spindle and to start the pump. When the pump is started, the carrier disk and the squeeze rollers supported thereon are also set in rotation if the hose is not yet inserted. The threading device simultaneously threads the hose inserted therein into the hose pump in the direction of a squeeze roller situated adjacent to the screw spindle.

In order to promote the automatic threading of the hose into the hose pump by means of the threading device, at least one guide roller is provided in addition to the squeeze rollers. It is preferred to provide several guide rollers that respectively are rotatably arranged on the carrier disk between adjacent squeeze rollers. On their outer circumference, the guide rollers feature a circumferential groove, into which the hose can engage. When the hose is guided downward in the direction of the carrier disk by the threading device, it engages into the groove on the outer circumference of the guide roller that currently lies adjacent to the threading device. The rotation of the carrier disk causes the guide roller arranged thereon to continue moving in the conveying direction of the pump such that it not only pulls the hose downward in the direction of the carrier disk, but also presses the hose radially outward against the abutment. As the carrier disk continues to rotate, the guide roller pulls the hose further into the hose pump along the inner circumference of the abutment with the shape of a segment of a circle due to the static friction on the hose surface and the frictional engagement in the groove on the outer circumference of the guide roller, namely until the carrier disk with the guide roller arranged thereon has carried out (nearly) one complete revolution and the hose is completely pulled into the hose pump due to the further rotation of the carrier disk. The rotation of the carrier disk ultimately causes the hose to be squeezed against the abutment by the squeeze roller that follows the guide roller on the carrier disk such that it is clamped between the squeeze roller and the abutment. During the further rotation of the carrier disk, this is also realized accordingly with the remaining guide rollers and squeeze rollers until the hose is completely pulled into the hose pump.

BRIEF DESCRIPTION OF THE DRAWINGS

Other advantages and characteristics of the invention result from the exemplary embodiment described below with reference to the attached drawings. In these drawings.

DETAILED DESCRIPTION OF THE INVENTION

Figure 1:
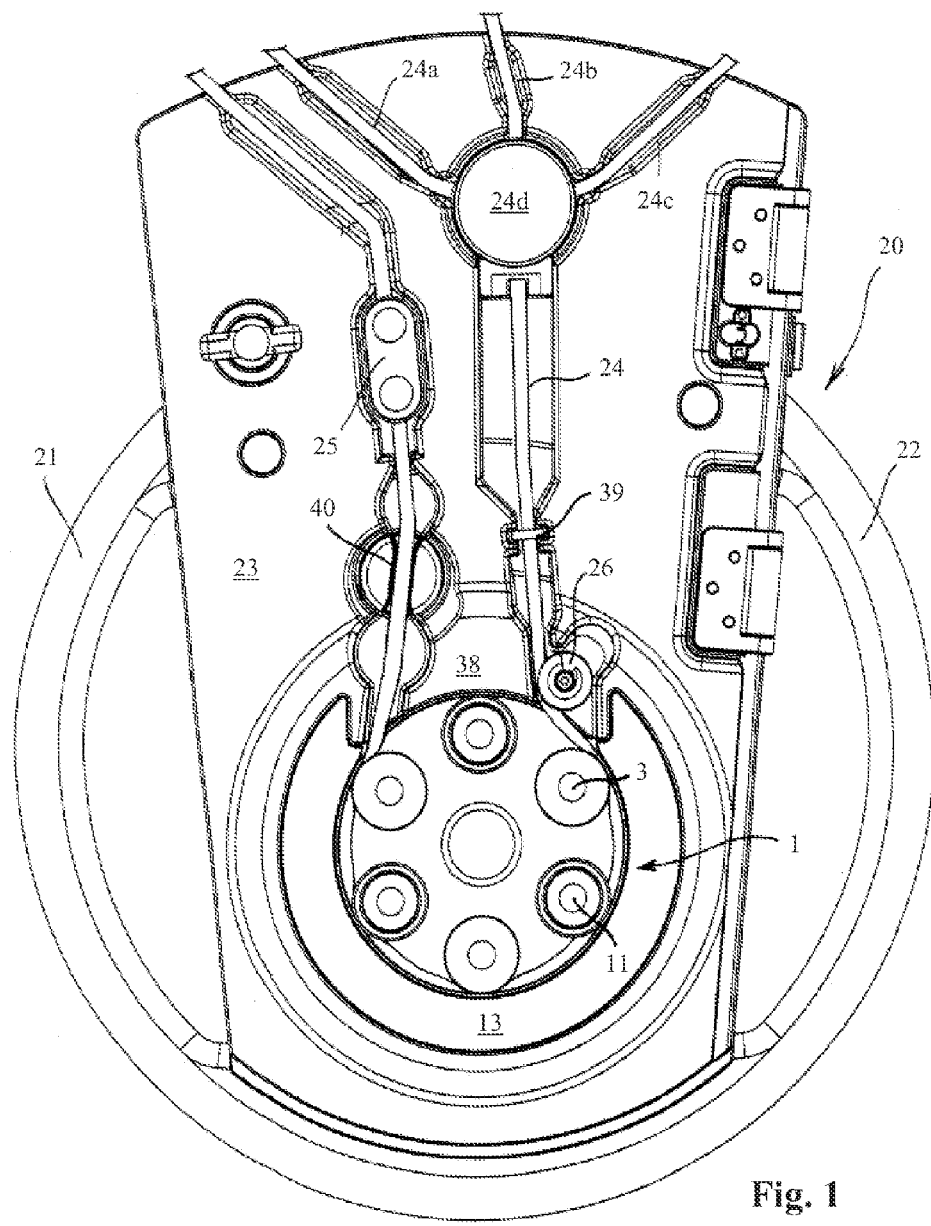
FIG. 1 shows a top view of an injection device, in which an inventive hose pump is used.

FIG. 1 shows the injection head of an injection device for injecting two different or identical contrast agents and a NaCl rinsing solution into the bloodstream of a patient, wherein an inventive hose pump 1 is utilized in said injection device. Such injection devices are used, e.g., for injecting contrast agents while carrying out imaging processes such as computer-assisted tomography, ultrasonic examinations and magnetic resonance tomography (MRT). The injection device comprises the injection head 20 illustrated in FIG. 1, in which the hose pump 1 is arranged. The injection head 20 comprises a plastic housing with two annular handles 21, 22. A panel 23 is arranged between the handles 21 and 22 and can be closed with a cover that is not illustrated in this figure. In its lower region, the panel 23 features a recess for accommodating the hose pump 1. Channel-shaped recesses 24, 25, into which a branched hose arrangement can be inserted, are situated above the aforementioned recess. The hose arrangement consists in particular, of a hose arrangement of the type described in detail in EP 2 011 541 A2. This hose arrangement comprises a total of three supply hoses, namely a first supply hose for a first contrast agent, a second supply hose for a second contrast agent and a third supply hose for a rinsing solution (particularly NaCl). The three supply hoses are connected to supply bottles for the contrast agent and the rinsing solution, which are also not illustrated in this figure, and inserted into the branches 24a, 24b and 24c of the recess 24 that are arranged in the upper region of the panel 23. A junction element inserted into the circular recess 24d of the panel 23 combines the three supply hoses connected to the supply containers into one hose section that is routed to the hose pump 1.

A threading device is provided for inserting the hose into the hose pump 1. The function and the design of this threading device are described below. The hose is ultimately routed through the hose pump 1 and placed into the recess 25 in the upper left part of the panel 23. The hose end is connected to a patient hose, through which the mediums carried in the hose can ultimately be injected into the bloodstream of the patient. A fixing device is provided for fixing the hose on the panel 23, wherein this fixing device makes it possible to fix the hose at a first location 39 on the intake side and at least one second location 40 on the output side of the hose pump. Ultrasonic sensors for detecting air bubbles in the hose are advantageously arranged at the fixing points 39 and 40. Other fixing points for fixing the hose on the panel 23 can be provided and are described, e.g., in EP 2011541 A1.

Figure 2:
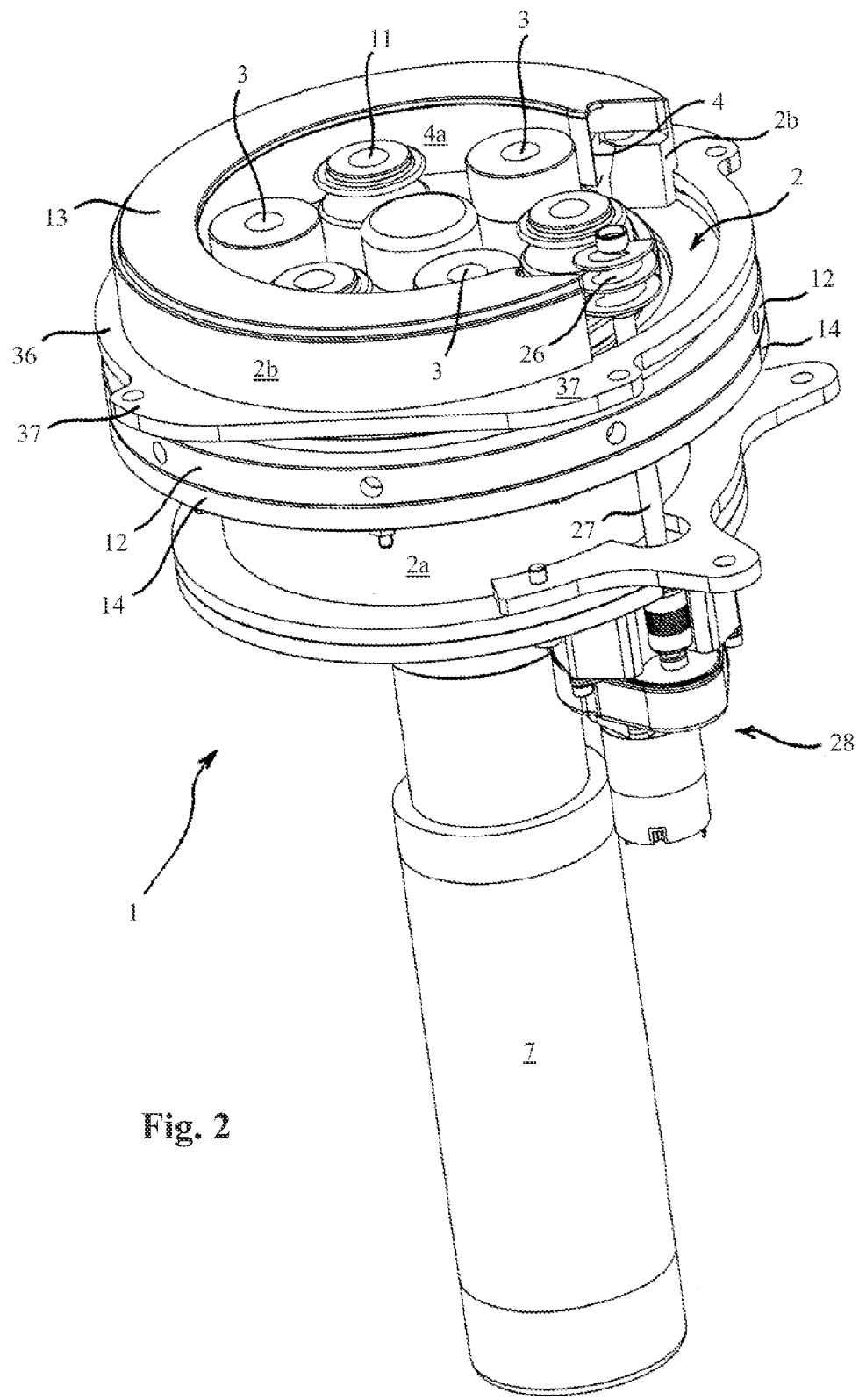
FIG. 2 shows a perspective representation of an inventive hose pump.
Figure 3:
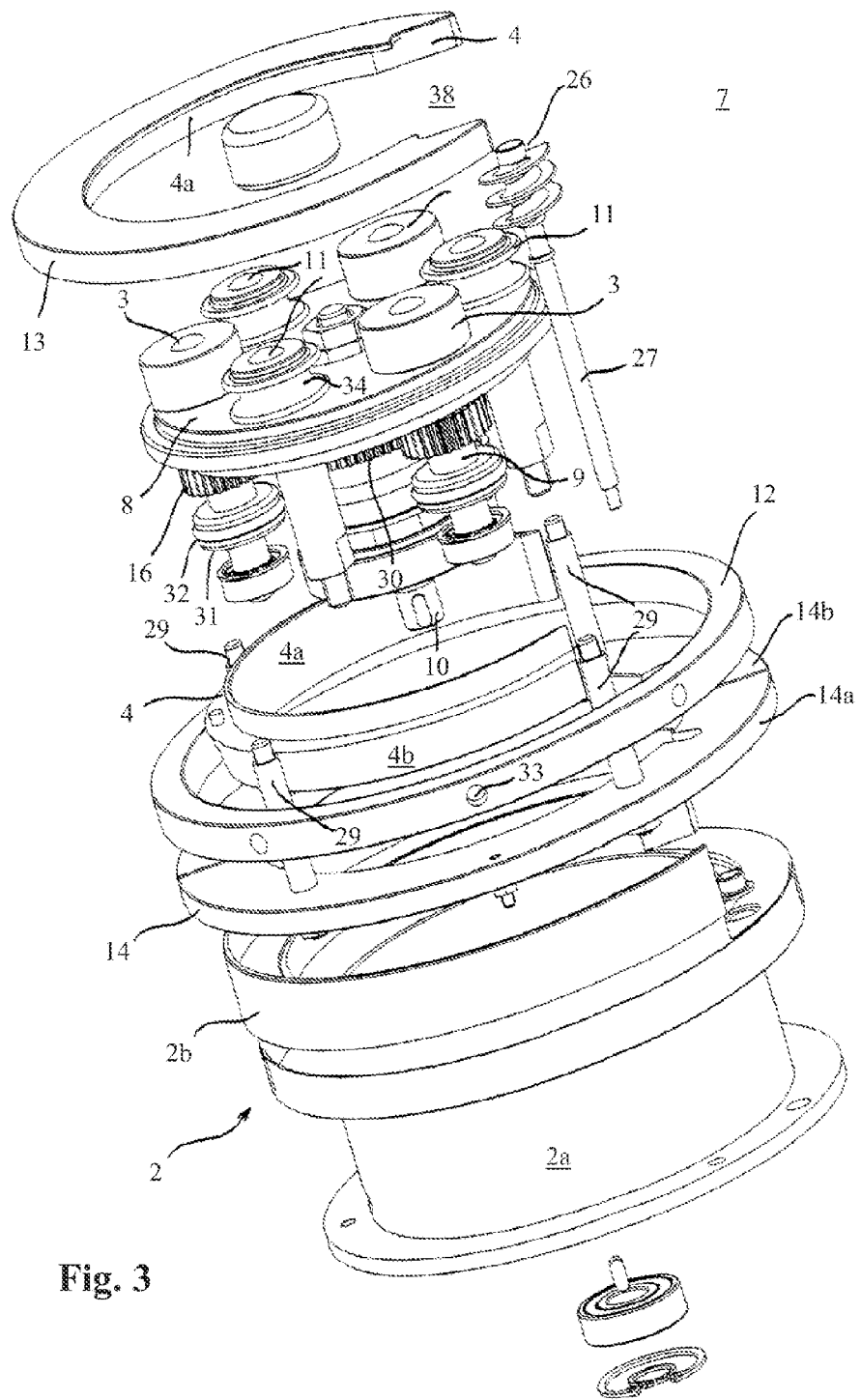
FIG. 3 shows an exploded view of the hose pump according to FIG. 2.

In FIGS. 2 and 3, the hose pump 1 is illustrated in detail in the form of a perspective representation, wherein FIG. 3 shows an exploded view. The hose pump 1 comprises a lower pump unit with a driving motor 7, as well as an upper pump unit with a housing 2. The housing 2 is divided into a lower housing part 2a and an upper housing part 2b. The lower housing part 2a and the upper housing part 2b may be realized integrally or in the form of two separate parts.

Figure 4A:
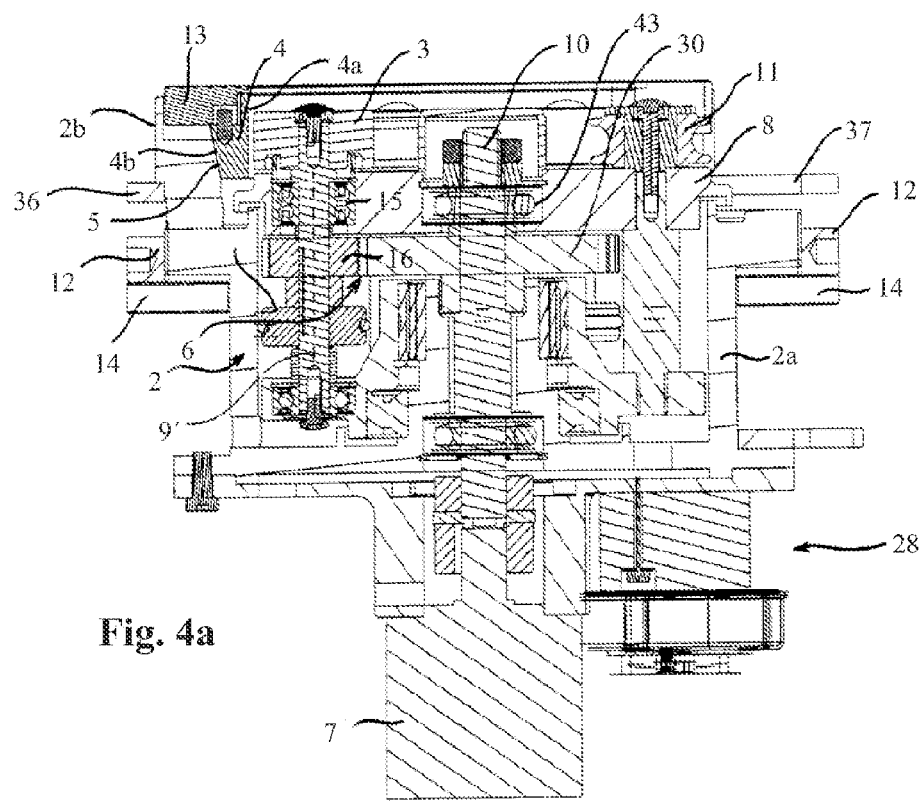
FIG. 4a shows a section through the hose pump according to FIG. 2 along the plane A-A.
Figure 4B:
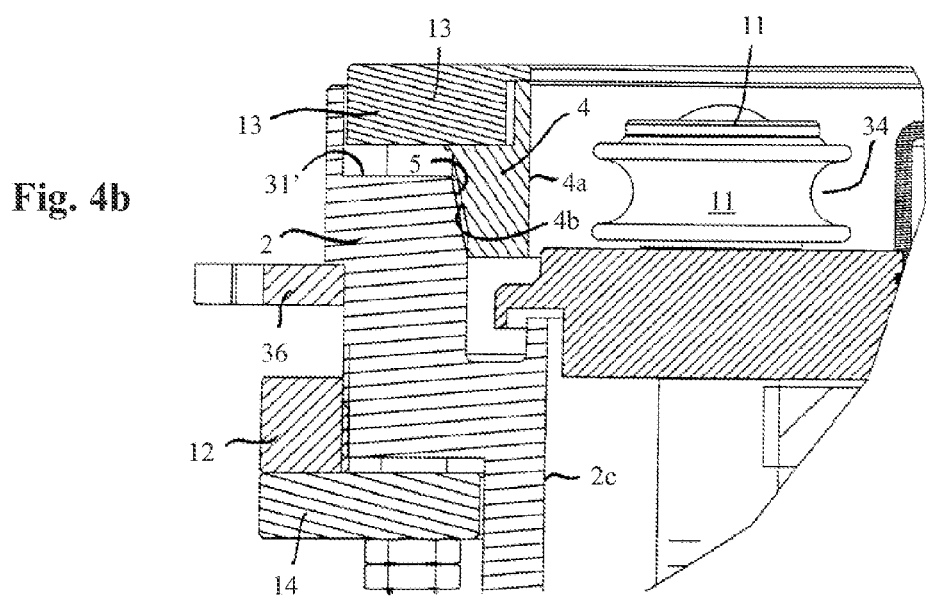
FIG. 4b shows a detail of a section through the hose pump according to FIG. 2 in the region of the abutment and a guide roller situated opposite the abutment.
Figure 5:
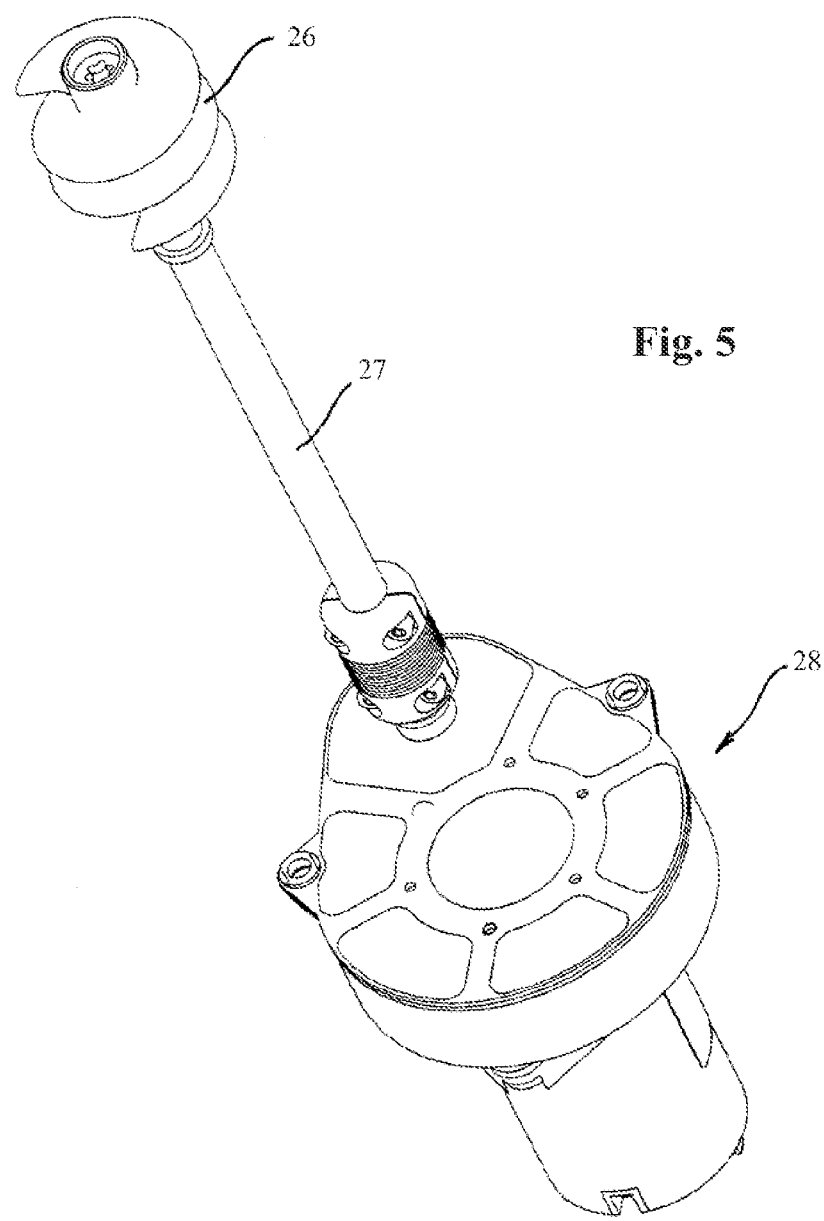
FIG. 5 shows a perspective representation of the threading device of the hose pump according to FIG. 2.

The lower pump unit comprises the driving motor 7 with a driveshaft 10 that is coupled to the upper pump unit via a gear mechanism. The design of the upper pump unit is illustrated in the form of a sectional representation in FIG. 4. A gear mechanism 6 coupled to the driveshaft 10 of the driving motor 7 is arranged in the interior of the housing 2. The gear mechanism comprises a sun wheel 30 that is connected to the driveshaft 10 of the driving motor 7 in a rotationally rigid fashion. The upper end of the driveshaft 10 is rotatably supported in a carrier disk 8 by means of a bearing 43. Several squeeze elements 3 are arranged on the carrier disk 8. In the exemplary embodiment shown, the squeeze elements 3 consist of driven squeeze rollers 3, wherein three squeeze rollers 3 of this type are uniformly arranged on the outer circumference of the circular carrier disk 8. The squeeze rollers 3 are rotatably supported on the carrier disk 8. For this purpose, each of the three squeeze rollers 3 is placed on a shaft 9 with an axis 9' and each shaft 9 is supported in a bore of the carrier disk 8 by means of a bearing 15. The shafts 9 and therefore the axes 9' of the squeeze rollers 3 extend parallel to the driveshaft 10 of the driving motor 7. During the operation of the pump, the driving motor 7 sets the carrier disk 8 and the squeeze rollers 3 in rotation via the gear mechanism 6. The gear mechanism 6 comprises planet wheels 16 in addition to the sun wheel 30, wherein such a planet wheel 16 is assigned to each squeeze roller 3 and fixed on the shaft 9 in a rotationally rigid fashion. Each of the planet wheels 16 is coupled to the sun wheel 30 of the planetary gear by means of a toothing. A friction wheel 31 is arranged on each shaft 9 adjacent to the planet wheel 16, wherein the friction wheel 31 is fixed on the shaft 9 in a rotationally rigid fashion and at a distance from the planet wheel 16. A circumferential groove 34 is arranged on the outer circumference of each friction wheel 31 and a rubber ring 32 (O-ring) is inserted into said groove. The friction wheel 31 is in contact with the inner circumference 2c of the pump housing 2 via this rubber ring 32. The inner circumference 2c of the housing 2 therefore acts as crown wheel of the planetary gear. When the driveshaft 10 is set in rotation by the driving motor 7, this rotary motion is transmitted to the shaft 9 via the coupling between the planet wheel 16 and the sun wheel 30 such that the shaft 9 and the squeeze roller 3 connected thereto in a rotationally rigid fashion are set in rotation. The friction wheel 31 simultaneously rolls on the inner circumference 2c of the pump housing 2, whereby the carrier disk 8 is likewise set in rotation relative the pump housing 2. Due to the friction wheels 31, the carrier disk 8 can also be set in rotation by the driving motor 7 if a hose is not yet inserted into the hose pump.

Guide rollers 11 are also supported on the carrier disk 8 in addition to the squeeze rollers 3. The guide rollers 11 serve for guiding the hose between adjacent squeeze rollers 3 and are not driven. On their outer circumference, the guide rollers 11 feature a groove 34 of semicircular cross section, in which the hose is guided. The arrangement of the guide rollers 11 and the squeeze rollers 3 on the carrier disk 8 is illustrated in particular in the exploded view according to FIG. 3.

In order to insert the hose into the hose pump, a threading device is provided that automatically threads the hose between the squeeze rollers 3 and the abutment 4. The threading device comprises a screw spindle 26 that is arranged outside the carrier disk 8. The screw spindle 26 is arranged on a shaft 27, wherein the shaft 27 extends parallel to the axis 9' of the squeeze rollers 3. The shaft 27 is rotatably supported in a housing part 2 of the hose pump and coupled to a spindle drive 28, by means of which the shaft 27 and the screw spindle 26 can be set in rotation in order to thread a hose placed into the screw spindle in the hose pump. The upper flights of the screw spindle 26 protrude over the upper side of the squeeze rollers 3 and the guide rollers 11 in the longitudinal direction of the hose pump (i.e., parallel to the axis of the respective shafts 10 and 27).

An abutment 4 is arranged on the upper end of the upper pump unit. The abutment 4 has the shape of a segment of a circle with a recess 38 and advantageously extends over an angular range of 200° to 300°. The screw spindle 26 is arranged in the region of the recess 38 of the abutment 4. The abutment 4 features an effective surface 4a that lies opposite the outer circumference of the squeeze rollers 3 and is spaced apart from this outer circumference by a distance d. The hose is threaded into the gap between the effective surface 4 and the outer circumference of each squeeze roller 3.

In order to insert the hose into the hose pump 1, the hose section to be inserted is initially fixed on the panel 23 at the two fixing points 39 and 40 by means of the fixing device. The hose section between the fixing devices 39 and 40 then has the shape of a loop (due to the natural twist of the hose section). The hose section is subsequently placed into the screw spindle 26. The pump is then set in motion such that the driving motor 7 rotates the carrier disk 8. The spindle drive 28 simultaneously sets the screw spindle 26 in rotation. For this purpose, the spindle drive 28 is coupled to the control of the driving motor 7. The rotation of the screw spindle 26 causes the screw spindle 26 to guide the hose downward in the direction of the carrier disk 8. Due to the rotation of the carrier disk, one of the guide rollers 11 is moved toward the hose and the hose engages into the groove 34 on the outer circumference of the guide rollers 11. As the carrier disk 8 continues to rotate, the guide roller 11 arranged thereon moves in the conveying direction of the pump and pulls the hose downward in the direction of the carrier disk 8 due to the frictional engagement in the groove 34 and simultaneously presses the hose radially outward against the abutment 4 due to the positive fit. As the rotation of the carrier disk 8 continues, the guide roller 11 pulls the hose further into the hose pump along the inner circumference of the abutment 4 with the shape of a segment of a circle due to the static friction on the hose surface and the frictional engagement in the groove 34 on its outer circumference, namely until the carrier disk with the guide roller 11 arranged thereon has carried out (nearly) one complete revolution and the hose has been completely pulled into the hose pump due to the continued rotation of the carrier disk. The rotation of the carrier disk ultimately causes the hose to be squeezed against the abutment 4 by the squeeze roller 3 that follows the guide roller 11 on the carrier disk 8. In this way, the hose is automatically inserted between the outer circumference of the squeeze rollers 3 and the abutment 4 and squeezed as the carrier disk 8 continues to rotate in order to convey the liquid carried therein.

Once the hose is completely inserted into the hose pump, the squeeze rollers 3 press the hose against the effective surface 4a of the abutment 4 during the operation of the hose pump (i.e., when the carrier disk 8 rotates and the squeeze rollers 3 rotate) in order to squeeze the hose diameter and thusly convey the medium in the hose onward in the conveying direction (i.e., in the rotating direction of the carrier disk 8).

After the pumping operation is completed, the threading device can also be used for unthreading the used hose during a required hose change. For this purpose, the spindle drive 28 rotates in the opposite rotating direction during the operation of the hose pump. Consequently, the screw spindle 26 pulls the hose section inserted into the hose pump upward such that the hose is disengaged from the groove 34 of the guide rollers 11. After one complete revolution of the carrier disk, the hose is completely pulled out of the hose pump, wherein the hose can be removed after loosening the fixing devices at the fixing points 39 and 40 and ultimately replaced with a new hose. A control routine for initiating the unthreading of the used hose is provided in the control of the spindle drive 28 and can be activated by the operator when a corresponding button is pushed.

In order to optimally adjust the distance between the abutment 4 and the squeeze rollers 3, the abutment with its effective surface 4a is in one preferred exemplary embodiment arranged on the housing 2 such that it can be displaced relative to the squeeze rollers 3. For this purpose, the abutment 4 is connected to a thrust collar 13. The thrust collar 13 also consists of a ring with the shape of a segment of a circle. The abutment 4 features an adjustment surface 4b that lies opposite the effective surface 4a. It is realized in a conical or cone-shaped fashion. The arrangement consisting of the abutment 4 and the thrust collar 13 is arranged in the upper opening of the housing 2 in such a way that the conical adjustment surface 4b of the abutment 4 is braced against a complementary (i.e., also conical or cone-shaped) support surface 5 on the housing 2, wherein the support surface 5 on the housing 2 conically widens (upper left side of FIG. 4) downward (i.e., into the housing interior).

A mounting ring 36 with mounting flanges 37 that is fixed on the housing (and not illustrated in FIG. 3 in order to provide a better overview) is provided on the outer side of the housing 2 in order to mount the housing 2 on the panel 23 of the injection head 20. An adjustment ring 12 is furthermore arranged on the outer side of the housing 2 in the transition area between the lower housing part 2a and the upper housing part 2b. The adjustment ring 12 consists of a circular ring that features an internal thread on its inner circular surface. An external thread realized complementary to this internal thread is provided on the outer side of the housing 2. The adjustment ring is coupled to the housing 2 by means of this thread arrangement in such a way that the adjustment ring can be continuously displaced in the axial direction between an uppermost position and a lowermost position referred to the housing 2 by turning the adjustment ring 12 relative to the housing 2. In order to turn the adjustment ring 12 relative to the housing 2, the outer circumference of the adjustment ring 12 is provided with several bores 33, into which a pin can engage.

A displacement ring 14 adjoins the underside of the adjustment ring 12. The displacement ring 14 is composed of two semicircular ring segments 14a and 14b and connected to the thrust collar 13 by means of several bolts 29 (FIG. 3).

The distance d between the squeeze rollers 3 and the effective surface 4a of the abutment 4 can be adjusted with the arrangement consisting of the abutment 4, the thrust collar 13, the displacement ring 14 and the adjustment ring 12.

In order to maximize the distance d between the outer circumference of the squeeze rollers 3 and the effective surface 4a, the abutment 4 is moved into its first (uppermost) position. Based on this position, the distance d can be reduced by turning the adjustment ring 12 on the housing 2 in the direction of its lowermost position. This causes the adjustment ring 12 to be displaced downward from its uppermost position. Consequently, the displacement ring 14 that adjoins the underside of the adjustment ring 12 is also displaced downward relative to the housing. Since the displacement ring 14 is connected to the thrust collar 13 by means of the bolts 29, the thrust collar 13 with the abutment 4 fixed thereon is also displaced downward. The adjustment surface 4b of the abutment 4 slides along the conical support surface 5 on the housing 2 in this case. During this motion, the abutment 4 with the shape of a segment of a circle slightly contracts and reduces its diameter such that the effective surface 4a is pressed toward the squeeze rollers 3 and the guide rollers 11 in the radial direction. This motion causes the distance d between the effective surface 4a and the outer circumference of the squeeze rollers 3 to be reduced. Once the adjustment ring 12 reaches its lowermost position, the underside of the thrust collar 13 rests on a base 31' of the housing 2. In this position, the minimum distance d between the effective surface 4a and the respective outer circumference of the squeeze rollers 3 and the guide rollers 11 is adjusted.

Due to this arrangement of the abutment 4, the gap size (i.e., the distance d) between the effective surface 4a and the outer circumference of the squeeze rollers 3 can be adjusted to an optimal value for the operation of the pump. This adjustment is initially carried out before the hose pump is put into service. A gauge, the thickness of which corresponds to the gap size to be adjusted, is advantageously inserted between the effective surface 4a and the outer circumference of the squeeze rollers 3 in order to adjust a desired distance d. Subsequently, the adjustment ring 12 is turned relative to the housing until the effective surface 4a and the outer circumference of the squeeze rollers 3 adjoin the outer surfaces of the gauge. If so required, the gap size can be readjusted when the hose pump is serviced.

The invention is not limited to the described exemplary embodiment. In an alternative embodiment of the invention, the second planet wheel can also be eliminated. In order to also set the carrier and the squeeze rollers supported thereon in rotation in this embodiment while the pump is running and a hose is not yet inserted, only one (first) planet wheel is assigned to each squeeze roller and coupled to the inner circumference of the housing that acts as crown wheel such that the carrier is set in rotation by the drive when the pump is running. The respective first planet wheel of each squeeze roller is advantageously coupled to the sun wheel via a toothing. The coupling with the inner circumference of the housing is realized via the external toothing arranged on the outer circumference of the respective planet wheel in this case. For this purpose, an internal toothing that is realized complementary to the external toothing of the planet wheel is provided on the inner circumference of the housing and meshes with the external toothing of the respective planet wheel. In this exemplary embodiment, the respective squeeze roller is set in rotation during the operation of the pump due to the coupling between the planet wheel and the sun wheel and the carrier is simultaneously set in rotation due to the coupling between the planet wheel and the inner circumference of the stationary housing. In this case, the internal toothing on the inner circumference of the housing act as crown wheel of a planetary gear that is composed of the sun wheel, the planet wheels and the stationary crown wheel.

Instead of the screw spindle, the threading device may also feature a gripper with a linear drive, wherein the gripper takes hold of or encompasses the hose or the hose section placed into the threading device and the linear drive subsequently guides the hose downward in the direction of the carrier disk such that it can be carried along by the guide rollers in the above-described fashion and inserted into the hose pump between the abutment and the squeeze rollers around the abutment. In this case, the linear drive may be realized in the form of a linear motor or a revolving cylinder engine with transmission gearing for converting the rotary motion into a linear motion. As an alternative to a motor drive, it would also be possible to use a bistable magnet for setting the threading device in motion and thusly inserting the hose into the pump. Furthermore, holding fins may be used instead of guide rollers, wherein said holding fins are arranged on the carrier plate and press the hose section inserted into the pump by the threading device downward in the direction of the carrier disk and radially outward in the direction of the abutment.

The inventive hose pump furthermore is not only suitable for use in injection devices, but also in other pump systems such as, e.g., infusion pumps.

The invention claimed is:

1. A hose pump for conveying a medium carried in a hose, the hose pump comprising:
    a housing with an inner circumference that acts as a crown wheel,
    a drive,
    several first planet wheels,
    several squeeze rollers, each of the several first planet wheels connected to a respective one of the several squeeze rollers in a rotationally rigid manner such that each of the several squeeze rollers can be driven by the drive via a gear mechanism with a sun wheel and a respective one of the several first planet wheels,
    wherein the rotating squeeze rollers press a hose inserted into the pump against an abutment during operation of the pump to squeeze the hose and thusly convey the medium in the hose onward in a conveying direction,
    wherein the hose pump includes several second planet wheels, with each of the several second planet wheels being a toothless friction wheel and each of the several second planet wheels is assigned to a respective one of the several squeeze rollers, and
    wherein
    the squeeze rollers are rotatably supported on a carrier that is rotatable relative to the housing
    the inner circumference of the housing is smooth, and
    each of the several second planet wheels frictionally engages the inner circumference of the housing to set the carrier in rotation by the drive during operation of the pump.

2. The hose pump according to claim 1, wherein the sun wheel is connected to a driveshaft of the drive in a rotationally rigid manner.

3. The hose pump according to claim 2, wherein torque transmitted from the driveshaft to the sun wheel is transmitted from the sun wheel and the second planet wheels to the carrier via the inner circumference of the housing, which is stationary, such that the carrier is also set in rotation during operation of the pump when no hose is inserted.

4. The hose pump according to claim 2, wherein the carrier is a carrier disk that is rotatably supported on the driveshaft of the drive by a bearing.

5. The hose pump according to claim 4, further including several squeeze roller shafts rotatably supported in the carrier disk, wherein an axis of each squeeze roller shaft extends parallel to the driveshaft of the drive and wherein each of the several squeeze rollers is arranged on a respective one of the several squeeze roller shafts.

6. The hose pump according to claim 1, wherein each of the several first planet wheels is in contact with the sun wheel via a toothing.

7. The hose pump according to claim 1, wherein each of the several second planet wheels is in contact with the inner circumference of the housing and rolls on the inner circumference during operation of the pump.

8. The hose pump according to claim 1, wherein each of the several second planet wheels is a friction wheel with a ring of elastomer material on its outer circumference and frictionally engaged with the inner circumference of the housing.

9. The hose pump according to claim 4, wherein a guide roller is positioned between two adjacent squeeze rollers on the carrier disk.

10. The hose pump according to claim 5, wherein a respective one of the several first planet wheels and a respective one of the several second planet wheels are arranged in a rotationally rigid manner on a respective one of the several squeeze roller shafts.

11. The hose pump according to claim 1, wherein the hose pump further comprises a threading device for inserting a hose between the squeeze rollers and the abutment.

12. The hose pump according to claim 11, wherein the threading device comprises a screw spindle that can be rotatively driven by a spindle drive.

13. The hose pump according to claim 12, wherein the spindle drive is coupled to the drive in such a way that the spindle drive sets the screw spindle in rotation as soon as the drive sets the carrier in rotation.

14. The hose pump according to claim 11, wherein the threading device automatically threads a hose inserted therein between the squeeze rollers and the abutment during operation of the hose pump.

15. The hose pump according to claim 11, further comprising a fixing device for fixing the hose inserted into the hose pump, wherein the fixing device enables fixing the hose at a first location on an intake side of the hose pump and at a second location on an output side of the hose pump.

* * * * *